(12) United States Patent
Adejare (10) Patent No.: US 8,703,799 B2
(45) Date of Patent: *Apr. 22, 2014

(54) NON-COMPETITIVE NMDA RECEPTOR ANTAGONISTS

(76) Inventor: Adeboye Adejare, Mantua, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/361,974

(22) Filed: Jan. 31, 2012

(65) Prior Publication Data

US 2012/0129889 A1 May 24, 2012

Related U.S. Application Data

(63) Continuation of application No. 11/820,524, filed on Jun. 19, 2007, now Pat. No. 8,129,414.

(60) Provisional application No. 60/805,164, filed on Jun. 19, 2006.

(51) Int. Cl.
*A61K 31/445* (2006.01)

(52) U.S. Cl.
USPC .......................................... 514/327; 524/329

(58) Field of Classification Search
USPC ................................. 514/327, 329
See application file for complete search history.

(56) References Cited

U.S. PATENT DOCUMENTS

| | | |
|---|---|---|
| 5,436,255 A | 7/1995 | Butler |
| 5,968,895 A | 10/1999 | Gefter et al. |
| 6,180,608 B1 | 1/2001 | Gefter et al. |

FOREIGN PATENT DOCUMENTS

WO PCT/US2007/014422 6/2007

OTHER PUBLICATIONS

Ferle-Vidovic et al., Synthesis and biological activity of phencyclideine and its adamantylamine derivatives, *European Journal of Medicinal Chemistry*, 1993, vol. 28, pp. 243-250.
Linders et al. (1993) *J. Med. Chem.* 36:2499-2507.
Thurkauf et al., (1990) *J. Med. Chem.* 33:2211-2215.
Johnson (1985) *Ann. Rep. Med. Chem.* 24, Chap. 5:41-50.
Kamenka et al., (1982) *J. Med. Chem.* 25: 431-435.
Kalir et al., (1969) *J. Med. Chem.* 12: 473-477.
Cone et al., (1984) *J. Pharmacol. Exp. Ther.* 228: 147-153.
Manallack et al. (1988) *Mol. Pharmacol.* 34: 863-879.
Bowen et al. (1993 ) *Mol. Neuropharmacol.* 3: 117-126.
Quirion et al. (1992) *Trends Pharmacol. Sci.* 13: 85-86.
Walker et al. (1990) *Pharmacol. Rev.* 42: 355-402.
Rogowski (1993) *Trends Pharmacol. Sci.* 14: 325-331.
Brennan (1996) *Chem Eng. News* 74: 41-45.
de Costa et al., (1992) *J. Med. Chem.* 35: 4704-4712.
Hays et al., (1993) *J. Med. Chem.* 36: 654-670.
Staley et al. (1996) *Psychopharmacology (Berl.)* 127: 10-18.
Keana et al. (1989) *Proc. Natl. Acad. Sci. USA* 86: 5631-5635.
Reynolds et al. (1992) *Eur. J. Pharmacol.* 226 53-58.
Chen et al. (1992) *J. Med. Chem* 35: 1634-1638.
Rajdev et al. (1993) *Br. J. Pharmacol.* 109: 107-112.

(Continued)

*Primary Examiner* — San-Ming Hui
(74) *Attorney, Agent, or Firm* — Fox Rothschild LLP (57) ABSTRACT

Disclosed herein are non-competitive NMDA receptor antagonists having chemical structures similar to that of phencyclidine (PCP). These antagonists contain a polycyclic ring structure in place of the cycloalkyl ring of PCP. The antagonists also differ from PCP in that they include an electron withdrawing group, a hydroxyl group, or an amine group at the para position of the phenyl ring. The antagonists disclosed herein are useful for treating or ameliorating a symptom of ailments associated with over excitation of cells (e.g., neurons) that express NMDA receptors. Examples of ailments that can be treated and for which symptoms can be ameliorated include epilepsy, neurodegenerative disease (e.g., Alzheimer's and Parkinson's diseases), drug addiction, neuropathic pain, and neuronal and glutamate-dependent tumors.

20 Claims, 3 Drawing Sheets

(56) References Cited

OTHER PUBLICATIONS

Reynolds et al. (1990) *Adv. Pharmacol.* 21: 101-126.
Ortwine (1994) ACS Satellite Television Seminar, "Molecular Modeling: The Small Molecule Approach," pp. 47-67.
Adejare and Sun (The 228th ACS National Meeting, Philadelphia, PA, Aug. 22-26, 2004, Abstract MEDI 67.
Sun and Adejare (*AAPS PharmSci 5*: Abstract M1127, Oct. 2003).
Watkins et al., 1993, in "The NMDA Receptors", Oxford University Press, Oxford, pp. 9-233.
Remington, 2006, *The Science and Practice of Pharmacy*, 21st Edition, Lippincott Williams & Wilkins, p. 25.
Rogers et al. (1995) *Biophys. J.* 68: 501-506.
Rzeski et al., 2001, *Proc. Natl. Acad. Sci. USA* 98 6372-6377.
Cavalheiro et al., 2001, *Proc. Natl. Acad. Sci. USA* 98: 5947-5948.
Remington, 2006, *The Science and Practice of Pharmacy*, 21st Edition, Lippincott Williams and Wilkins, p. 1418.

NON-COMPETITIVE NMDA RECEPTOR ANTAGONISTS

CROSS-REFERENCES TO RELATED APPLICATIONS

This application is a continuation of U.S. patent application Ser. No. 11/820,524, filed Jun. 19, 2007, which claims priority under 35 U.S.C. §119(e) to U.S. Provisional Patent Application Ser. No. 60/805,164, filed Jun. 19, 2006. The contents of the foregoing applications are hereby incorporated by references in their entireties.

STATEMENT REGARDING FEDERALLY SPONSORED RESEARCH OR DEVELOPMENT

This work was supported in part by grants from the National Institutes of Health (Grants Nos. 2R15NS3693-03A1 and 7R15N536393-04) and the U.S. Government may therefore have certain rights in this invention.

BACKGROUND OF THE INVENTION

The invention relates generally to the field of non-competitive NMDA receptor antagonists that are analogs of phencyclidine (PCP). These compounds contain a polycyclic ring structure in place of the cycloalkyl ring of PCP, as well as an electron withdrawing group, hydroxyl or amino group at the para position of the phenyl ring. The antagonists disclosed herein are useful for ameliorating, treating, and preventing ailments associated with detrimental effects attributable to "over-activation" of NMDA receptors on cells of various types, such as over-excitation of neurons having NMDA receptors.

Neuronal damage, including brain damage, can occur via over-excitation of neurons. When over-excitation occurs, the membrane potential collapses and that can lead to cell death. The N-methyl-D-aspartate (NMDA) receptor appears to have a role in neurodegeneration that occurs by means of this mechanism. When over-activated, the NMDA receptor allows excess calcium ions (i.e., $Ca^{2+}$) to flow into the neuron bearing the receptor, causing both necrosis and apoptosis of the neuron.

Figure 1:
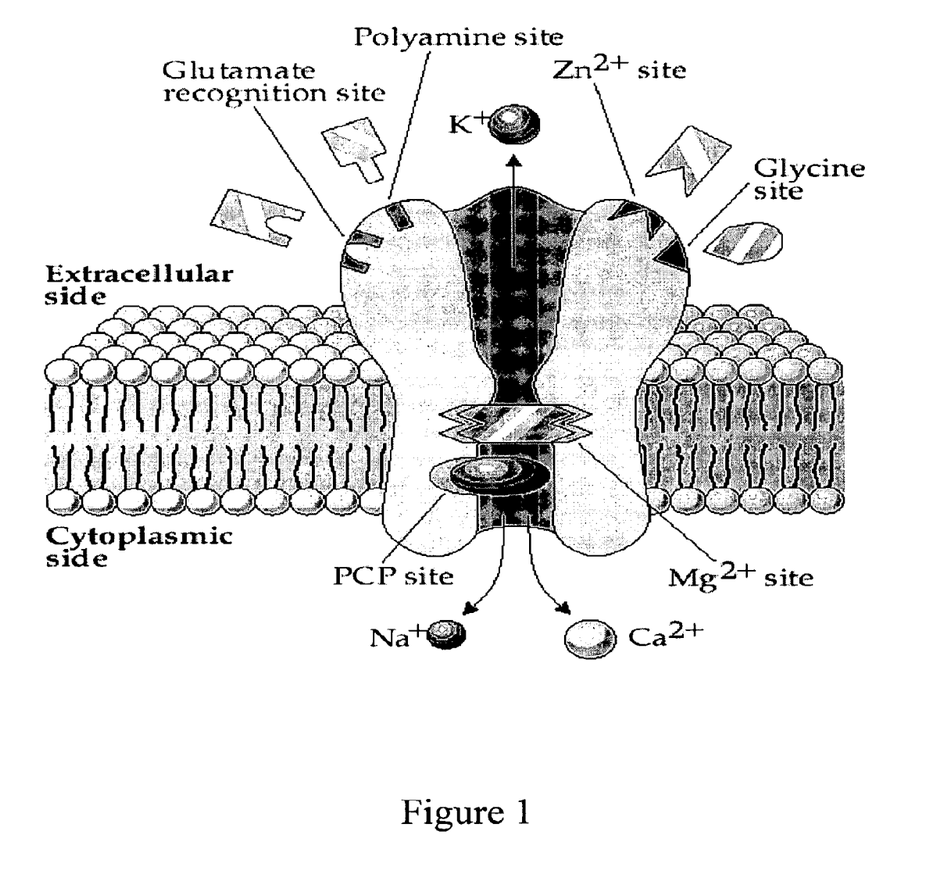
FIG. 1 shows a current model of the NMDA receptor, as described by Watkins et al., 1993, in "The NMDA Receptors", Oxford University Press, Oxford, pp. 9 to 233.

The NMDA receptor is a transmembrane protein located on neuronal cells and has multiple ligand binding sites, including sites for glutamate, glycine, polyamine and cations (e.g., $Zn^{2+}$ and $Mg^{2+}$) and phencyclidine (PCP) binding as shown schematically in FIG. 1.

Rogawski reports that NMDA receptor channel blockers may act as neuroprotective agents. As illustrated in FIG. 1, PCP acts as a non-competitive antagonist of the NMDA receptor by binding in the ion channel thereof and blocking the inflow of calcium ions into the neuron. However, PCP does not selectively interact with the NMDA receptor; PCP binds with other neuronal receptors, including sigma (a) receptors and cholinergic (nicotinic) receptors. PCP also inhibits uptake of biogenic amines (including dopamine, norepinephrine and epinephrine) and interacts with voltage-gated potassium channels.

The multiple and various interactions and activities of PCP are thought to induce the well-known side effects of PCP ingestion, which include psychosis and ataxia. These side effects and the high abuse potential of PCP significantly limit the practical therapeutic value of this compound.

The psychotic and ataxic effects associated with PCP appear to be mediated by PCP binding to a receptors. It has been recognized in the art that compounds that selectively bind to the PCP binding site of the NMDA receptor (relative to the PCP binding site of the a receptor or other neuronal receptors) might be useful neuroprotective agents. Such compounds can act as selective, non-competitive antagonists of NMDA receptor function. The literature proposes that development of PCP analogs might provide useful therapeutic agents for treatment of neurodegenerative conditions associated with over activation of NMDA-bearing cells such as neurons in neurodegenerative conditions. However, data demonstrating the efficacy of any such analogs or types of analogs for this purpose have been lacking prior to this disclosure.

The present disclosure overcomes those shortcomings by providing NMDA receptor antagonism data for compounds designed based on structure-function analyses of PCP which were undertaken by the present investigators in order to identify potentially efficacious therapeutic agents that inhibit NMDA receptor activity.

PCP has three moieties: a phenyl ring, a 6-membered cycloalkyl ring and a piperidine (cyclic amine) moiety, arranged as shown below:

Many PCP analogs are known and have been described. See, for example, Linders et al., 1993, J. Med. Chem. 36: 2499-2507; Thurkauf et al., 1990, J. Med. Chem. 33: 2211-2215; Johnson, 1985, Ann. Rep. Med. Chem. 24, Chap. 5; Kamenka et al., 1982, J. Med. Chem. 25: 431-435; Kalir et al., 1969, J. Med. Chem. 12: 473-477; Cone et al., 1984, J. Pharmacol. Exp. Ther. 228: 147-153; Manallack et al., 1988, Mol. Pharmacol. 34: 863-879; Bowen et al., 1993, Mol. Neuropharmacol. 3: 117-126; Quirion et al., 1992, Trends Pharmacol. Sci. 13: 85-86; Walker et al., 1990, Pharmacol. Rev. 42: 355-402; Rogawski, 1993, Trends Pharmacol. Sci. 14: 325-331; Brennan, 1996, Chem. Eng. News 74: 41-45; de Costa et al., 1992, J. Med. Chem. 35: 4704-4712; Hays et al., 1993, J. Med. Chem. 36: 654-670; Staley et al., 1996, Psychopharmacology, Berl., 127: 10-18; Keana et al., 1989, Proc. Natl. Acad. Sci. USA 86: 5631-5635; Reynolds et al., 1992, Eur. J. Pharmacol. 226: 53-58; Chen et al., 1992, J. Med. Chem. 35: 1634-1638; Rajdev et al., 1993, Br. J. Pharmacol. 109: 107-112; Reynolds et al., 1990, Adv. Pharmacol. 21: 101-126; and Ortwine, 1994, ACS Satellite Television Seminar, "Molecular Modeling: The Small Molecule Approach," pp. 47-65.

Adejare and Sun (The 228th ACS National Meeting, Philadelphia, Pa., Aug. 22-26, 2004, Abstract MEDI 67) report the synthesis and chemical characterization of two classes of fluorinated PCP analogs. In one class, the phenyl ring is replaced with a 2-fluorophenyl group, the cycloalkyl group with a bicycloalkyl group, and the amine is variously a free amine, pyrrolidine or piperidine. In the other class, the phenyl moiety is also replaced by a 2-fluorophenyl group and the amine is variously a free amine, pyrrolidine or piperidine. However, in this group, the cycloalkyl group is a cyclopentyl or cyclohexyl group. Although this report speculates that these PCP analogs might act as selective NMDA receptor antagonists, no suggestive or confirming data is provided.

Sun and Adejare (AAPS PharmSci 5: Abstract M1127, October 2003) describe synthesis of nine PCP analogs, each having same bicycloalkyl group, namely a bicyclo[2.2.1]heptyl group. The remainder of the molecules have the phenyl ring as a phenyl, 3-fluorophenyl or 4-fluorophenyl group with the amine moiety being a free amine, pyrrolidine or piperidine. These nine PCP analogs are also speculated to potentially act as selective NMDA receptor antagonists, but again no suggestive or confirming data is provided.

Without structure-function correlations, i.e., without pharmacological or biological data, the selectivity of PCP analogs for NMDA and σ receptors cannot be accurately predicted, nor can potential therapeutic efficacy of such analogs. For example, after assessing the biological activity of some of the PCP analogs described by Adejare and Sun (2004) and Sun and Adejare (2003), it was subsequently discovered by the present investigators that many of the compounds disclosed in those references are toxic and unsuitable for therapeutic use. The present disclosure is based, in part, on the unexpected finding that PCP analogs having more constrained alkyl rings (i.e., those having multiple cyclic alkyl rings) and para-substituted phenyl rings exhibit suitable activity and have significantly less toxicity while exhibiting neuroprotective action. As such, the present disclosure significantly advances the knowledge in this field.

BRIEF SUMMARY OF THE INVENTION

Disclosed herein are methods for using selective NMDA receptor antagonists to treat or ameliorate ailments associated with over-excitation of neurons and NMDA receptors. In certain embodiments, such methods comprise administering an antagonist to a subject for a time and in an amount sufficient to inhibit activity of an NMDA receptor. Such inhibition can occur, for example, by blocking the ion channel and preventing calcium influx into the cell. The methods described herein include use of antagonists having one of at least three general chemical formulas.

Certain of the antagonists suitable for use in the methods disclosed herein contain a bicyclo[2.2.1]heptyl ring and are represented by the formula referred to herein as Structure A

(A)

Other antagonists suitable for use in the methods disclosed herein contain a bicyclo[2.2.2]octyl ring and are represented by the formula referred to herein as Structure B (B)

Still other antagonists suitable for use in the methods disclosed herein contain an adamantane moiety (multiple six-membered alkyl rings) and are represented by the formula referred to herein as Structure C (C)

In each of Structures A, B, and C, the R moiety can be an electron withdrawing group, a hydroxyl group or an amino group. For example, R can be a halo moiety such as a fluorine atom, a nitrate moiety, or a halomethyl moiety such as a fluoromethyl group. In these three Structures, the cycloalkyl ring can have one or more of the poly-cyclic ring hydrogen atoms independently substituted with a lower alkyl group, such as a methyl or ethyl group. Use of pharmaceutically acceptable salts of these compounds is expressly contemplated.

When R is an electron withdrawing group, R can be a halo moiety (i.e., a fluoro, chloro, bromo, or iodo atom), a nitrate moiety, or a halomethyl group, such as a fluoromethyl group (including mono-, di-, and tri-fluoromethyl groups), for example. When the cyclic ring is a bicyclo[2.2.1]heptyl ring (i.e., Structure A) and R is a fluoro group, then the compound is 1-(2-(4-fluorophenyl)bicyclo[2.2.1]hept-2-yl)piperidine, also referred to herein as "bicyclo,4-F-PCP."

The antagonists and methods disclosed herein are useful for treating, ameliorating, and preventing conditions associated with "over-activation" of NMDA receptors on cells of various types, such as neurons and glutamate-dependent tumor cells. Such conditions are known in the art to include cerebral ischemia, stroke, brain trauma, brain tumors, Alzheimer's disease, Parkinson's disease, epilepsy and other convulsive disorders, schizophrenia, acute and chronic neuropathic pain, sleep disorders, drug addiction (e.g., addiction to morphine and other opiates), the psychological aspects of depression, vision disorders (e.g., retinal disorders such as macular degeneration), ethanol withdrawal, anxiety, memory dysfunction, learning disabilities, and neurofibromatoses (e.g., neurofibromatosis type 1 {a.k.a. NF1} and memory- and learning-deficiencies associated therewith).

By way of example, the compositions and methods described herein can be used to treat, ameliorate, or prevent convulsions or other symptoms associated with epilepsy in a subject. This is achieved by administering to the subject an NMDA receptor antagonist disclosed herein for a time and in an amount sufficient to inhibit or reduce the symptom. For example, the subject can be treated with bicyclo, 4-F-PCP. By way of further example, the antagonists described herein can be used to treat, ameliorate, slow, arrest, or prevent neurodegenerative disorders, such as Alzheimer's disease and Parkinson's disease. Such use entails delivering one or more of the antagonists to the affected or at-risk cells of a subject afflicted with, suspected of being afflicted with, or at risk for developing the disorder. Such delivery can be achieved by any of a variety of routes, such as oral administration of a solid or liquid composition including the antagonist, by injection of a composition including the antagonist, or by local implantation of a sustained-release composition including the antagonist.

The invention also includes the NMDA receptor antagonists described herein and pharmaceutical formulations containing those antagonists. In accordance with U.S. and other national laws pertaining to packaging, sale, and use of pharmaceutically active agents, the compositions described herein can be formulated, packaged, and labeled for use in prevention, amelioration, or treatment of the conditions described herein.

DETAILED DESCRIPTION OF THE INVENTION

General Description and Definitions

Disclosed herein are selective NMDA receptor antagonists and methods for using the antagonists to treat, ameliorate, or prevent conditions and/or ailments associated with over-activation of NMDA receptors. Such methods involve administering an NMDA receptor antagonist of the type described herein, or a pharmaceutically-acceptable salt thereof, to a subject for a time and in an amount sufficient to inhibit activity of that receptor and/or reduce a physiological consequence of activation of the receptor, such as neuronal stimulation resulting from activation of NMDA receptors on neurons. The antagonists disclosed herein are represented by the chemical formulas shown in Structures A, B, and C.

Structures A, B, and C are (A)

(B)

(C)

In each of Structures A, B, and C, the R moiety is an electron withdrawing group, a hydroxyl group or an amino group. The cycloalkyl rings of any of Structures A, B, and C (i.e., the bicyclo[2.2.1]heptyl rings of Structure A, the bicyclo [2.2.2]octyl rings of Structure B, and the rings of the adamantane moiety of Structure C) can have a lower alkyl group, such as a methyl or ethyl moiety independently substituted in place of one or more of the ring hydrogen atoms.

The term "electron-withdrawing group" is known in the art and denotes the tendency of a substituent to attract valence electrons from neighboring atoms, i.e., the substituent is electronegative with respect to neighboring atoms. Examples of electron-withdrawing groups include nitro, acyl, formyl, alkylsulfonyl, arylsulfonyl, trifluoromethyl, cyano, halo (e.g., fluoro, chloro, bromo, and iodo) moieties, and other electron-withdrawing groups are known. In embodiments described herein, halo, nitrate and fluoromethyl groups ($CF_3$, $CHF_2$ or $CH_2F$) are disclosed as suitable electron withdrawing groups.

Instead of being an electron withdrawing group, R can instead be a hydroxyl or an amino group. In certain embodiments, hydroxyl or amino R groups are included both for therapeutic efficacy, and because they can provide reactive intermediates for the synthesis of compounds described herein that include electron withdrawing groups as the R moiety. For example, compounds wherein R is an amino group can be converted to compounds wherein R is an acetamide group.

As used herein, "lower alkyl" means branched- and straight-chain, saturated aliphatic hydrocarbon groups having from 1 to 6 carbon atoms. Lower alkyl groups include methyl, ethyl, n-propyl, isopropyl, n-butyl, isobutyl, tert-butyl, all pentyl isomers and all hexyl isomers. Suitable lower alkyl groups include methyl and ethyl groups.

Synthesis of Antagonists and their Pharmaceutically-Acceptable Salts

Figure 2:
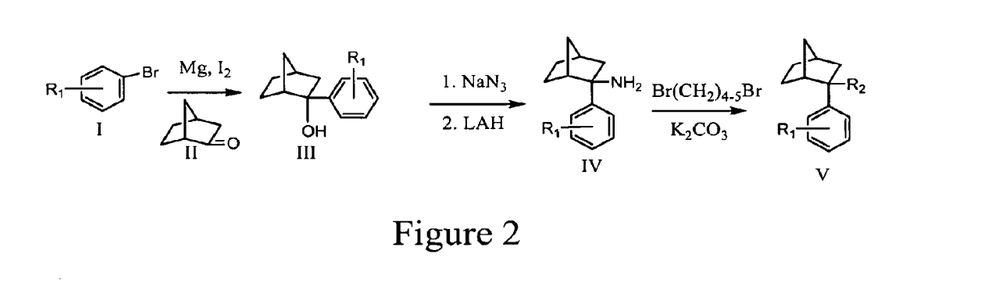
FIG. 2 illustrates a scheme for synthesizing certain of the NMDA receptor antagonists disclosed herein.

The antagonists disclosed herein can be synthesized by the general scheme shown in FIG. 2 or by adaptation thereof. For example, a Grignard reaction can be used to react the appropriate polycyclic ring ketone precursor with a 1-bromo-4-substituted benzene (e.g., 1-bromo-4-fluorobenzene or 1-bromo-4-trifluoromethylbenzene) to produce tertiary alcohols corresponding to compound III of FIG. 2. Those alcohols are converted to the corresponding amines (compound IV of FIG. 2) by reaction with sodium azide followed by reduction with lithium aluminum hydride (LAH). The amines are reacted with 1,5-dibromopentane to produce the corresponding piperidine analogs. The amine hydrochloride salts can be prepared by bubbling hydrogen chloride through the ethyl ether solutions (or other appropriate solvents) of the amines.

Methods for purification and characterization of the antagonists, such as crystallization or preparative chromatography, are also well known to those of skill in the art. For example, the crude mixtures can be purified by preparative thin layer chromatography (TLC) with a mobile phase composed of chloroform and ethyl ether (9:1). Desirable solvents for crystallization include chloroform and hexane, but appropriate solvents can be readily determined by those of skill in the art.

Pharmaceutically-acceptable salts of the antagonists can be prepared by reacting the free acid or base forms of these compounds with a stoichiometric or greater amount of the appropriate base or acid in water or in an organic solvent, or in a mixture of the two; generally, non-aqueous media like ether, ethyl acetate, ethanol, isopropanol, or acetonitrile are particularly well-suited. These salts can also be prepared by ion exchange.

Pharmaceutical Formulations

An antagonist disclosed herein can be made or formulated as a pharmaceutically-acceptable salt. "Pharmaceutically-acceptable" salts are well known in the art and refer to derivatives of the disclosed compounds that include acid or base cations or salts. Examples include mineral or organic acid salts of the basic residue of the piperidine moiety or of any basic residue on the substituted phenyl ring (e.g., the amine moiety of an antagonist wherein R is an amine group). Other examples include alkali or organic salts of acidic residues on the phenyl ring.

Pharmaceutically-acceptable salts can include sulfate, pyrosulfate, bisulfate, sulfite, bisulfite, phosphate, ammonium, monohydrogen phosphate, dihydrogen phosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, hippurate, maleate, butyne-1,4-dioate, hexyne-1,6-dioate, benzoate, chlorobenzoate, methylbenzoate, dinitrobenzoate, hydroxylbenzoate, methoxybenzoate, phthalate, sulfonate, xylenesulfonate, phenylacetate, phenylpropionate, phenylbutyrate, citrate, lactate, α-hydroxybutyrate, glycolate, maleate, tartrate, methanesulfonate, propanesulfonate, naphthalene-1-sulfonate, napthalene-2-sulfonate, mandelate, magnesium, tetramethylammonium, potassium, trimethylammonium, sodium, methylammonium, calcium, and like salts. Lists of suitable salts are found in, for example, Remington, 2006, The Science and Practice of Pharmacy, 21st Edition, Lippincott Williams & Wilkins.

An antagonist disclosed herein can exist as a single stereoisomer, or as a mixture of stereoisomers. For example, the antagonist can be made and used in the form of an enantiomer or as a racemic mixture of enantiomers. Similarly, pure and mixed diastereomers can be made and used. The pharmaceutical compositions described herein can include an individual (i.e., substantially purified) stereoisomer, mixtures of stereoisomers, and racemic mixtures thereof. Methods of screening stereoisomers for toxicity and efficacy are described herein and are otherwise well known in the art. In view of the known stereoselectivity of many cell-surface receptors, it is foreseeable that NMDA receptors will exhibit binding preference (i.e., lower $K_i$ value) for one stereoisomer of each antagonist described herein, relative to another stereoisomer. Although the preferred stereoisomer is not immediately predictable a fortiori, comparison of binding (and antagonism) ability of stereoisomers is routine in the art and can be performed using the assays described herein or as otherwise known in the art.

An antagonist disclosed herein can be formulated as a pharmaceutical composition comprising one or more of the antagonists described herein together with a pharmaceutically-acceptable carrier. Suitable pharmaceutical carriers are described, for example, in Remington: The Science and Practice of Pharmacy, 21st Edition (Lippincott Williams & Wilkins, 2006). Pharmaceutically-acceptable carriers can be sterile liquids, such as water and oils, including those of petroleum, animal, vegetable or synthetic origin, such as peanut oil, soybean oil, mineral oil, and sesame oil. In particular embodiments, water is an advantageous carrier, such as when the pharmaceutical composition is administered intravenously. Likewise, saline solutions, aqueous dextrose, and glycerol solutions are similarly advantageous in certain embodiments, particularly for injectable solutions. If a particular antagonist exhibits relatively low solubility in aqueous systems, any of a wide variety of alternative pharmaceutically acceptable solvents and additives are known that can improve the solubility of the antagonist in the vehicle desired for delivery. By way of example, the antagonist can be dissolved and/or suspended in an alcohol (e.g., ethanol) solution or in a composition including DMSO or a detergent.

In addition to the pharmacologically active agent, the pharmaceutical compositions described herein can include suitable pharmaceutically-acceptable carriers, such as those comprising excipients and auxiliaries to facilitate processing of the active compounds into formulations for delivery to the site of action. Suitable formulations for parenteral administration include aqueous solutions of the active compounds in water-soluble form; for example, water-soluble salts. Oily injection suspensions of the active compounds may also be administered. Suitable lipophilic solvents or vehicles include fatty oils, such as sesame oil or synthetic fatty acid esters (e.g., ethyl oleate or triglycerides). Aqueous injection suspensions can contain substances that increase the viscosity of the suspension. These include, for example, sodium carboxymethyl cellulose, sorbitol, and dextran. Optionally, the suspension can also contain stabilizers. The compositions can also include solubilizing agents (e.g., cyclodextrins) for improving the amount of the antagonist(s) dissolved (i.e., rather than suspended) in a liquid component of the composition. Liposomes can also be used to encapsulate the agent for delivery into the cell, and can improve delivery of an antagonist described herein across the blood-brain barrier. Improved delivery of an antagonist across the blood-brain barrier can also be achieved by administering a composition including the antagonist having a very small (e.g., micronized) form of the compound.

The pharmaceutical formulation for systemic administration as disclosed herein can be formulated for enteral, parenteral or topical administration. Indeed, all three types of formulations can be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

The antagonists described herein can also be incorporated into pharmaceutical compositions which allow for sustained delivery of those compounds to a mammal for a period of several days, several weeks, or a month or more. Such formulations are described, for example, in U.S. Pat. Nos. 5,968,895 and 6,180,608 and are otherwise known in the art. Any pharmaceutically-acceptable, sustained-release formulation known in the art is contemplated.

For topical administration, any common topical formulation such as a solution, suspension, gel, ointment, salve, or similar composition can be employed. Preparations of such topical formulations are described in the art of pharmaceutical formulations as exemplified, for example, by Remington, 2006, The Science and Practice of Pharmacy, 21st Edition, Lippincott Williams & Wilkins. For topical application, the antagonists as disclosed herein can be administered as a powder or spray, particularly in aerosol form, for example.

The active ingredient can also be administered in pharmaceutical compositions adapted for systemic administration. If a drug is to be administered systemically, it can be confected as a powder, pill, tablet or other solid composition or as a syrup, elixir or other liquid composition for oral administration. For intravenous, intraperitoneal or intra-lesional administration, the active ingredient is prepared as a solution or suspension capable of being administered by injection. In certain cases, it may be useful to formulate the active ingredient in suppository form or as an extended release formulation for deposit under the skin or intramuscular injection.

The antagonists described herein can be administered by inhalation. For inhalation therapy, the compound can be in a solution useful for administration by metered dose inhalers or in a form suitable for a dry powder inhaler, for example.

Pharmaceutical compositions expressly include both those formulated and intended for ethical administration to humans and veterinary compositions formulated and intended for administration to non-human animals.

Therapeutic, Preventative, and Ameliorative Applications

Described herein are methods of treating, ameliorating, preventing, or some combination of these, conditions associated with over activation of NMDA receptors. "Over-activation" of NMDA receptors on a cell means occurrence of one or more physiological consequences of NMDA receptor binding with glutamate (or aspartate) to an extent or degree that a pathological condition results. By way of example, many neurological disorders (including neurodegenerative disorders such as Alzheimer's and Parkinson's diseases) are attributable to over activation of cells bearing NMDA receptors. Likewise, it is known that certain glutamate-dependent tumors rely on NMDA receptor activation for their continued survival.

These methods involve administering one or more NMDA receptor antagonists of the type described herein (or a pharmaceutical composition including such an antagonist) to a subject afflicted with such a condition. The antagonist(s) are administered for a duration of time and in an amount sufficient to inhibit activity of the receptor and to thereby reduce, prevent, or eliminate the corresponding pathological condition or a symptom of that condition. The antagonists used in these methods are those PCP analogs described herein—i.e., those having constrained cycloalkyl rings (i.e., having polycyclic alkyl rings), a para-substituted phenyl ring, and a piperidine moiety. Such compounds are represented by Structures A, B, and C, as described herein. Bicyclo,4-F-PCP is an example of an antagonist suitable for use in these methods.

It is contemplated that the antagonists described herein can be administered in the form of one or more prodrugs which, upon administration to a subject, are metabolized or otherwise acted upon by the normal (or pathological) biochemical processes of the subject's body to yield an antagonist described herein. By way of example, an ester or amide of an antagonist described herein can be administered to a subject, the ester or carboxylic acid group thereof being removed in the subject's body, yielding the active antagonist. Design and synthesis of activatable prodrugs is routine and within the ken of the skilled artisan in this field, and the methods described herein for administering the antagonists described herein include administration of corresponding prodrugs.

The antagonists disclosed herein are capable of interacting with or binding with the NMDA receptor (presumably at or near the PCP binding site of the receptor) to significantly reduce or prevent influx of cations, especially calcium cations, mediated by the receptor. Binding activity can be assessed in vitro, if needed, by assay techniques known to those of skill in the art. Likewise, calcium and cation flux assays in neuronal cells are well known, see, e.g., Rogers et al. (1995) Biophys. J. 68:501-506. In the methods described herein, one or more antagonists is administered to a subject afflicted with, believed to be afflicted with, or at risk for affliction with a disorder described herein. The antagonist is administered in an effective amount, such an effective amount being an amount sufficient to alleviate, eliminate, or prevent at least one symptom of the disorder. An effective amount can also be viewed as the amount of antagonist that reduces, eliminates, or prevents a physiological consequence of activation of the receptor, such as neuronal over-stimulation resulting from over-activation of NMDA receptors on neurons.

The neurological conditions treatable in accordance with antagonists and methods disclosed herein are those that are associated with over-excitation of neurons and/or the NMDA receptor. These conditions include cerebral ischemia, stroke, brain trauma, brain tumors, Alzheimer's disease, Parkinson's disease, epilepsy, schizophrenia, acute neuropathic pain, chronic neuropathic pain, sleep disorders, drug addiction, depression, certain vision disorders, ethanol withdrawal, anxiety, and memory and learning disabilities. When measured in rat and mouse models, the antagonists disclosed herein exhibit anti-convulsive activity and this demonstrates that compositions including such antagonists are suitable for treating epilepsy and other conditions associated with convulsions. This also demonstrates that oral administration of such antagonists results in delivery to brain tissue (i.e., across digestive and blood-brain barriers) of an amount of antagonist sufficient to treat, alleviate, or prevent chronic conditions such as neurodegenerative disorders, in that the amount of antagonist required for alleviation of acute conditions such as convulsions is expected by a skilled artisan to be much (e.g., about 2-fold to 10-fold or more) higher than the amount necessary for chronic conditions.

In one embodiment, the methods described herein are used to treat or ameliorate convulsions or other epileptic activity in a subject experiencing (immediately or intermittently) such activity. Such methods involve administering a composition including one or more of the NMDA receptor antagonists described herein to the subject for a time and in an amount sufficient to inhibit or reduce the convulsions or activity. Bicyclo,4-F-PCP is a suitable compound for use in this embodiment.

Tumors can be treated, or their symptoms ameliorated, using the NMDA receptor antagonists disclosed herein. Rzeski reported colon adenocarcinoma, astrocytoma, and breast and lung carcinoma cells are sensitive to the anti-proliferative effect of the NMDA antagonist dizocilpine. Rzeski also reported that breast and lung carcinoma, colon adenocarcinoma, and neuroblastoma cells responded favorably to the amino-3-hydroxyl-5-methyl-4-isoxazole-propionate antagonist (AMPA) GYKI52466. Rzeski et al., 2001, Proc. Natl. Acad. Sci. USA 98:6372-6377. Cavalheiro reported that the NMDA antagonist dizocilpine (MK-801) and the AMPA antagonist GYKI52466 limit proliferation of cancer cells in a wide variety of human non-neuronal cancers, including not only colon, breast, lung, and thyroid carcinoma, but also glial and neuronal tumors, such as astrocytoma, neuroblastoma, and medulloblastoma/rhabdomyosarcoma. Cavalheiro et al., 2001, Proc. Natl. Acad. Sci. USA 98:5947-5948. According to both research groups, the anti-proliferative effect was attributable to decreased cell division and increased cell death. Further, both groups reported that the anti-proliferative effect of glutamate antagonists is calcium dependent, which is consistent with the known calcium permeability of glutamate receptor/ion channel complexes. Several other NMDA and AMPA receptor antagonists exhibit anti-cancer activity, evidencing involvement of NMDA and AMPA receptors in these tumors.

The compositions described herein are useful in methods of treating glutamate-dependent tumors, ameliorating the symptoms of such tumors, or both. Such methods involve administering a composition including one or more NMDA receptor antagonists of the type described herein to a subject having such a tumor. The composition including the antagonist is administered for a time and in an amount sufficient to ameliorate one or more symptoms associated with the glutamate-dependent tumor. Such symptoms include, for example, convulsions associated with or occurring because of the presence of brain tumors. Any measurable change in the tumor, such as shrinkage, or changes in cognitive or motor abilities (for neuronal tumors, including brain tumors) can be monitored to assess efficacy. Additionally or alternatively, methods of treating glutamate-dependent tumors independently include administering the antagonists for a time and in an amount to relieve pain associated with those tumors. Pain relief is thus another measure of efficacy of the antagonists.

Examples of glutamate-dependent tumors include non-neuronal tumors such as colon adenocarcinoma, breast, lung, and thyroid tumors. Glial and neuronal tumors, such as astrocytoma, neuroblastoma, and medulloblastoma/rhabdomyosarcoma are also examples of glutamate-dependent tumors.

One way to measure the anti-cancer (or anti-tumor) effect of the NMDA receptor antagonists disclosed herein is to observe morphological alterations in tumor cells. Such alterations may include reduced membrane ruffling and pseudopodial protrusions. Likewise, decreased motility and decreased invasive growth of tumor cells can be monitored. Since convulsions are often associated with symptoms of brain tumors, assessing the level and frequency of convulsions provides another measure of efficacy that can be monitored. Assessment of the morphological, motility-inhibiting, and growth-inhibiting activities of the antagonists described herein can be performed using either or both of in vitro and in vivo model systems known in the art, and such assessments are within the ken of the ordinarily-skilled artisan in this field.

The antagonists disclosed herein (as well as their pharmaceutically-acceptable salts and compositions including the same) can be administered to a wide variety of subjects. As used herein, subjects expressly include humans, laboratory animals (e.g., mice, rats, non-human primates, rabbits, and pigs), and domesticated or farm animals (e.g., cats, dogs, cattle, horses, swine, sheep, goats, fish, lizards, and chickens and other birds).

As used herein, the term "administering" includes dispensing, delivering, or otherwise applying a compound disclosed herein in a method disclosed herein, e.g., in a pharmaceutical formulation, to a subject by any suitable route for delivery of that compound to the desired location in the subject. Expressly contemplated approaches include delivery by either the parenteral or oral route, intramuscular injection, subcutaneous/intradermal injection, intravenous injection, buccal administration, transdermal delivery and administration by the rectal, colonic, vaginal, intranasal or respiratory tract route (e.g., by inhalation).

It is contemplated that the compounds disclosed herein are administered in an effective amount, that being an amount sufficient to achieve a desired result, e.g., sufficient to inhibit activity of NMDA receptors for cells bearing such receptors (e.g., to reduce neuronal stimulation of NMDA receptor-bearing neurons). Reduction of neuronal stimulation can be assessed directly (e.g., by assessing neuronal cells in vitro) or by assessment of a symptom (e.g., frequency, duration, or severity of convulsions) or other characteristic (e.g., memory retention) of neuronal stimulation. An therapeutically beneficial amount of an antagonist described herein is an amount for which any toxic or detrimental effects associated with administration of the amount of the compound are outweighed by the therapeutically beneficial effects associated with such administration. For example, for the treatment of epilepsy, a therapeutically beneficial amount is an amount that inhibits or reduces convulsions (e.g., frequency, duration, or severity of such convulsions) or other symptoms associated with epilepsy (such as frequency, duration, or severity of petit mal seizures). For treatment of tumors, a therapeutically beneficial amount is an amount that leads to improvement of a tumor characteristic in the subject, and such tumor characteristics include reduction of tumor size, lessening of frequency or duration of tumor-related convulsions, prolonged survival, improvement in cognitive or motor abilities, reduction of tumor-associated pain, or any other measure available to assess tumor status in the subject.

Effective amounts of the compounds used in the methods described herein can vary according to factors such as the disease state, age, and weight of the subject, and the ability of the compound to elicit a desired response in the subject. Dosage regimens can be adjusted to provide the optimum therapeutic response.

Suitable dosages for the compounds and methods disclosed herein range from about 0.05, 0.1, 0.2 or 0.5 mg/kg body weight to about 100 or 200 mg/kg body weight. In certain embodiments, dosages range from about 0.5 to 1 mg/kg body weight to about 100 mg/kg body weight. In other embodiments doses range from about 10 to about 50 mg/kg body weight. Performance of studies to determine an optimal dosage for a particular condition using a particular compound is well within the level of ordinary skill in this field. The $ED_{50}$, for example, of bicyclo,4-F-PCP in rats for amelioration of electrically-induced convulsions is 28 mg/kg (milligrams of compound per kilogram of subject body weight), as described herein in Example 2. As would be understood by a skilled artisan in this field, it is reasonable to expect that the $ED_{50}$ of an antagonist described herein would be significantly (e.g., about 2-fold to 10-fold or more) lower for alleviation, treatment, or prevention of a chronic condition, such as neurodegeneration associated with Alzheimer's disease or Parkinson's disease than for chronic conditions (which require much more of the antagonist) such as convulsions. For example, the $ED_{50}$ of bicyclo,4-F-PCP for alleviation, treatment, or prevention of Alzheimer's and Parkinson's disease would be expected to be on the order of 3 mg/kg.

EXAMPLES

The invention is now described with reference to the following Examples. These Examples are provided for the purpose of illustration only, and the invention is not limited to these Examples, but rather encompasses all variations which are evident as a result of the teaching provided herein.

Example 1

Synthesis of PCP Analogs

The following materials were used to synthesize the antagonists disclosed herein: norcamphor (Lancaster), 4-bromofluorobenzene (99%), lithium aluminum hydride (LAH), ammonium hydroxide (28-30%), diethyl ether, hydrochloric acid (37.4%), $H_2SO_4$, sodium chloride, chloroform, N,N-dimethylformamide (99.9%), sodium azide (99%), 1,4-dibromobutane (97%), 1,4-dibromopentane, chloroform-d, THF (Fisher), and magnesium turnings. THF was distilled over sodium, and injected by syringe under a dry nitrogen atmosphere.

Instrumentation and Methods

Melting points were determined on a MEL-TEMP II capillary melting point apparatus. MS spectra were collected with electrospray method using a FINNIGAN TSQ-700 mass spectrometer. NMR spectra were obtained on a VARIAN 300/54 300 MHz spectrometer. $^1H$ and $^{13}C$ NMR spectra were recorded in $CDCl_3$ and respectively referred to internal TMS (0 ppm) and $CDCl_3$ (77 ppm) signals. $^{19}F$-NMR spectra were obtained in $CDCl_3$ using $CFCl_3$ as internal standard (0 ppm). All reported values are δ values in ppm. Column chromatographic separations were performed over ACROS gel No. 7631-86-9, particle size 35-70 μm. Preparative thin layer chromatography (TLC) separations were performed on ANALTECH UNIPLATE silica gel GF 20 cm×20 cm preparative TLC plates.

The compounds shown in Table 1 were synthesized according to the general reaction scheme shown in FIG. 2. Briefly, norcamphor (compound II in FIG. 2) was reacted with a Grignard reagent of 1-bromobenzene, 1-bromo-3-fluorobenzene or 1-bromo-4-fluorobenzene (compound I in FIG. 2) to produce the corresponding 2-(fluoro-phenyl)-bicyclo[2.2.1]heptan-2-ols (compound III in FIG. 2). These alcohols were converted to the corresponding amines using sodium azide and LAH to produce compounds 1, 2 and 3 listed on Table 1 (compound IV in FIG. 2). The crude amines were reacted with 1,4-dibromobutane or 1,5-dibromopentane to produce the corresponding pyrrolidine analogs (compounds 5, 7 and 9; Table 1) or piperidine analogs (compounds 4, 6 and 8; Table 1), respectively (compound V in FIG. 2). The detailed synthesis and characterization of compounds 2 and 4 is provided below.

TABLE 1

| Compound V Substituents (See FIG. 2) | | |
|---|---|---|
| Compound | $R_1$ | $R_2$ |
| 1 | 3'-F | $NH_2$ |
| 2 | 4'-F | $NH_2$ |
| 3 | H | $NH_2$ |
| 4 | 4'-F |  |
| 5 | 4'-F |  |
| 6 | 3'-F |  |
| 7 | 3'-F |  |
| 8 | H |  |
| 9 | H |  |

Synthesis of (±) 2-(4-fluorophenyl)-bicyclo[2.2.1]
heptan-2-ol (III)

A mixture of 1-bromo-4-fluorobenzene (5.00 ml, 45.5 mmol), magnesium turnings (3.32 g, 137 mmol), and a few iodine crystals in 70 ml dry THF were vigorously stirred for 4 hours under the protection of nitrogen and cooling with ice/water. Norcamphor (5.00 g, 45.5 mmol) dissolved in 10 ml dry THF was added drop-wise, and the reaction was allowed to warm up to room temperature and stirred overnight. The reaction was carefully quenched with water and decanted from the excess magnesium turnings. The reaction mixture in THF and water was adjusted to pH 7 with 2N HCl solution and extracted with chloroform (3×50 ml). The extract was dried over anhydrous sodium sulfate and the solvent was removed by vacuum evaporator. This resulted in an alcohol intermediate (III) appearing as a faintly yellow oil (9.4 g, 99%).

Synthesis of (±)-2-(4-fluorophenyl)-bicyclo[2.2.1]
hept-2-ylamine (2)

The alcohol intermediate III (9.4 g, 46 mmol) was dissolved in dry chloroform (100 ml), and the flask soaked in ice/water. Sodium azide (8.89 g, 137 mmol) was added to the mixture, followed by trifluoroacetic acid (30.5 ml, 410 mmol) added in a drop-wise manner over a 20 minute period. The mixture was stirred overnight, warmed to room temperature, and quenched with water and 80 ml saturated $Na_2CO_3$. The reaction mixture was extracted with $CHCl_3$ (3×80 ml), dried over anhydrous sodium sulfate and evaporated. This resulted in a crude tertiary azide appearing as a pale yellow oil (10.5 g).

The azide (10.5 g, 45.4 mmol) was dissolved in 20 ml dry THF, and then added drop-wise over a 30 minute period to a solution of lithium aluminum hydride (2.60 g, 68 mmol) in 40 ml dry THF while the mixture was cooled in ice/water. The reaction was quenched with ice after 10 hours, and the slurry was vacuum filtered. The mixture was extracted with diethyl ether (3×40 ml). Then, the mixture was further extracted with 2N HCl solution (2×30 ml), and the ethereal solution discarded. The acidic solution was adjusted to pH 9 with saturated ammonia solution before it was again extracted by diethyl ether (3×40 ml). The ethereal layer was dried over anhydrous sodium sulfate and evaporated. This resulted in 2-(4 fluorophenyl)-bicyclo[2.2.1]heptan-2-amine (compound 2; Table 1), which appeared as a clear oil (6.6 g, 69%). This oil (0.4 g) was purified by preparative TLC using a mixture of chloroform and diethyl ether (9:1, v/v) as mobile phase.

An off-white oil resulted from the purification, and after cooling off and crystallizing, the compound was characterized as follows by $^1$H NMR (CDCl$_3$): δ 7.2 (m, 2H, 3' and 5' Ar—H); 6.8 (m, 2H, 2' and 4' Ar—H); 1.0-2.6 (b, 10H, 4-CH$_2$ and 2CH); $^{13}$C NMR (CDCl$_3$): δ 163.0 (s, 1C, 4'-C); 160.4 (s, 1C, 1'-C); 128.6 (s, 1C, 5'-C); 128.5 (s, 1C, 3'-C); 115.3 (s, 1C, 6'-C); 115.0 (s, 1C, 2'-C); 63.6 (s, 1C, 1×4° C.); 48.7 (s, 1C, 1CH); 45.6 (s, 1C, 1CH); 37.1 (s, 1C, 1CH$_2$); 36.8 (s, 1C, 1CH$_2$); 28.7 (s, 1C, 1CH$_2$); 24.7 (s, 1C, 1CH$_2$); $^{19}$F NMR (CDCl$_3$): δ −117.6 ppm. MS (ESI) (m/z, species, %): 206, [M+1], 10; 189, [M−16], 100.

Synthesis of (±) 1-[2-(4-fluorophenyl)-bicyclo[2.2.1]hept-2-yl]-piperidine (compound 4; Table 1)

Anhydrous potassium carbonate (0.94 g, 6.8 mmol) and 1,5-dibromopentane (0.47 ml, 3.4 mmol) were added to a crude base of (±) 2-(4-fluoro-phenyl)-bicyclo[2.2.1]hept-2-ylamine (compound 2; Table 1) (0.70 g, 3.4 mmol) in dry DMF (30 ml). The mixture was heated to 50° C. and incubated for 8 hours. The mixture was then stirred overnight at room temperature and subsequently quenched with water. The resultant mixture was extracted with chloroform (3×20 ml). The chloroform extracts were combined and the chloroform was removed using a rotary evaporator. The remaining residue was extracted with ether (2×25 ml), and the ethereal extract was washed with water (2×20 ml) and dried over anhydrous sodium sulfate. A pale yellow oil was obtained after removing the ether. Purification by TLC with a mobile phase of chloroform and diethyl ether (9:1) resulted in a colorless crystalline compound (0.65 g, 70% yield, m.p. 58-59° C.).

The amine hydrochloride was synthesized by bubbling hydrogen chloride gas through the ethyl ether solution of (±)1-(2-(4-fluorophenyl)bicyclo[2.2.1]hept-2-yl)piperidine to give colorless crystals (m.p. 86-88° C.). The solvent used for crystallization was a mixture of methanol and ethyl ether.

The resultant free amine was characterized as follows by $^1$H NMR (CDCl$_3$): δ 7.0-7.1 (m, 4H, 4 Ar—H); 1.0-2.3 (b, 20H, 9CH$_2$ and 2CH); $^{13}$C NMR (CDCl$_3$): δ 162.8 (s, 1C, 4'-C); 160.8 (s, 1C, 1'-C); 130.6 (s, 1C, 5'-C); 130.5 (s, 1C, 3'-C); 113.8 (s, 1C, 6'-C); 113.6 (s, 1C, 2'-C); 72.7 (s, 1C, 1×4° C.); 47.6 (s, 2C, 2CH$_2$); 41.9 (s, 1C, 1CH); 41.7 (s, 1C, 1CH); 37.0 (s, 1C, 1CH$_2$); 35.2 (s, 1C, 1CH$_2$); 30.2 (s, 1C, 1CH$_2$); 27.3 (s, 2C, 2CH$_2$); 24.7 (s, 1C, 1CH$_2$); 25.3 (s, 1C, 1CH$_2$); $^{19}$F NMR (CDCl$_3$): δ −118.4 ppm. MS (ESI) (m/z, species, %): 274, [M+1], 100.

Example 2

MES Test for Anti-Convulsive Activity

The maximal electroshock (MES) test was used to initially screen compounds for anti-convulsive activity in mice.

In the MES test, 50 mA of 60 MHz alternating current was delivered to 19-25 g mice for 2 s by a corneal electrode which had been primed with an electrolyte solution containing an anesthetic agent (0.5% tetracaine HCl). Mice were tested at various intervals following doses of 30, 100 or 300 mg/kg of test compound given by i.p. injection in 0.01 ml/g of the aqueous carrier. Animals are considered protected from MES-induced seizures upon abolition of hindlimb tonic extensor component of the seizure (Swinyard et al. 1989; White et al. 1995a; White et al. 1995b).

Acute toxicity was assessed by monitoring animals for overt signs of impaired neurological or muscular function. The rotorod test measures minimal motor impairment (MMI) by placing mice on a rod rotated a 6 rpm. A compound is considered toxic if the mice fall off the rod three times during a 1-min period. Additionally, mice were observed and noted for circular or zigzag gaits, abnormal body posture and spread of the legs, tremors, hyperactivity, lack of exploratory behavior, somnolence, stupor, catalepsy, loss of placing response and change in muscle tone.

The results for the MES protection test and toxicity are shown in Table 2. For activity, (+) means MES test protection occurred at 100 mg/kg delivered i.p. in mice and (−) means that no activity was observed. For toxicity, (+++) means some animals died at 100 mg/kg and all animals died at 300 mg/kg; (++) means that some toxicity observed at 100 mg/kg and all animals died at 300 mg/kg; and (−) means no toxicity observed at 100 mg/kg and some observed at 300 mg/kg but no animals died at 300 mg/kg.

TABLE 2

MES activity in Mice

| Cmpd. No. | Cycloalkyl | Phenyl | Amine | Activity | Toxicity |
|---|---|---|---|---|---|
| 2 | bicyclo[2.2.1] | 4-F | amine | + | ++ |
| 3 | bicyclo[2.2.1] | H | amine | − | +++ |
| 4 | bicyclo[2.2.1] | 4-F | piperidine | + | − |
|   | bicyclo[2.2.1] | H | ether | + | ++ |
|   | cycloheptyl | 4-F | piperidine | + | +++ |
|   | cycloheptyl | 2-F | amine | + | ++ |

The ether substituent in Table 2 is N—(—O—CH$_2$CH$_2$) piperidine. Based on these results, it appears that a constrained or rigid alkyl ring, a para-substituted phenyl ring and piperidine are necessary for activity and reduced toxicity.

Compound 4 (Bicyclo,4-F-PCP) was tested in rats using 30 mg/kg delivered orally. The ED$_{50}$ (effective dose) was determined to be 28.33 mg/kg when administered to rats by this route. Additionally, log P (i.e., a measure of lipophilicity) of bicyclo,4-F-PCP was determined to be 2.07, the pKa 8.87 and the solubility of the fumarate salt thereof in aqueous solution was determined to be 0.0366 M or 14.2 mg/ml.

Example 3

MK-801 (Dizocilpine) Binding Site Assay

NMDA receptors were isolated from rat forebrain membrane (B$_{max}$=830 fmol/mg protein) and incubated with $^3$H-labeled MK-801 maleate (15-30 Ci/mmol) in 20 mM HEPES (pH 7.5) buffer at 25° C. for 90 min to yield labeled receptors. MK-801 is a known non-competitive antagonist of NMDA receptor.

Selected concentrations of non-labeled bicyclo,4-F-PCP were incubated with the labeled receptors in 20 mM HEPES (pH 7.5) buffer at 25° C. for 90 min. At the conclusion of the assay, the reaction mixture was filtered immediately on glass filters by vacuum filtration and washed twice with buffer solutions. The radioactivity trapped on the filters was measured, compared with controls, and the $k_i$ and $IC_{50}$ values of bicyclo,4-F-PCP were calculated.

Figure 3:
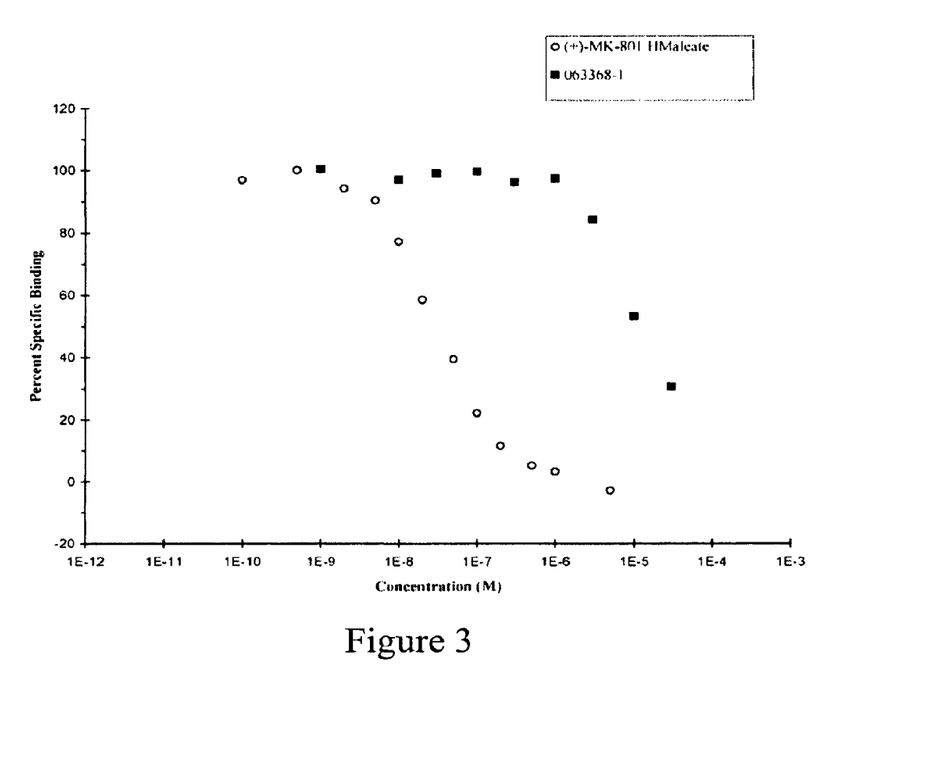
FIG. 3 illustrates the ability of bicyclo,4-F-PCP to compete with MK-801 (dizocilpine) for binding to the NMDA receptor. In the figure, data corresponding to the maleate salt of MK-801 are shown as open circles, and data corresponding to bicyclo,4-F-PCP (designated "063368-1" in the figure) are shown as closed squares. The vertical axis represents specific binding percentage, and the horizontal axis represents molar concentration of the respective compound.

As shown in FIG. 3, bicyclo,4-F-PCP can displace [$^3$H] MK-801 maleate bound to NMDA receptors. This data demonstrates that bicyclo,4-F-PCP can compete with MK-801 and bind inside of the NMDA receptor ion channel at non-competitive sites. This evidence reinforces the conclusion that bicyclo,4-F-PCP and related compounds are noncompetitive NMDA receptor antagonists.

Example 4

NMDA Agonist Binding Site Assay

NMDA receptors were isolated from rat forebrain membrane ($B_{max}$=0.77 pmol/mg tissue) and incubated with $^3$H-labeled CGP 39653 (15-30 Ci/mmol) in 50 mM TRIS-acetate (pH 7.4) buffer at 0-4° C. for 60 min to yield labeled receptors. CGP 39653 is a known competitive antagonist of NMDA receptor.

Selected concentrations of non-labeled bicyclo,4-F-PCP were incubated with the labeled receptors in 50 mM TRIS-Acetate (pH 7.4) buffer at 0-4° C. for 60 min. At the conclusion of the assay, the reaction mixture was immediately filtered using glass filters and vacuum filtration, washing twice with buffer solutions. The radioactivity trapped on the filters was measured, compared with controls, and the $k_i$ and $IC_{50}$ values of bicyclo,4-F-PCP calculated.

Figure 4:
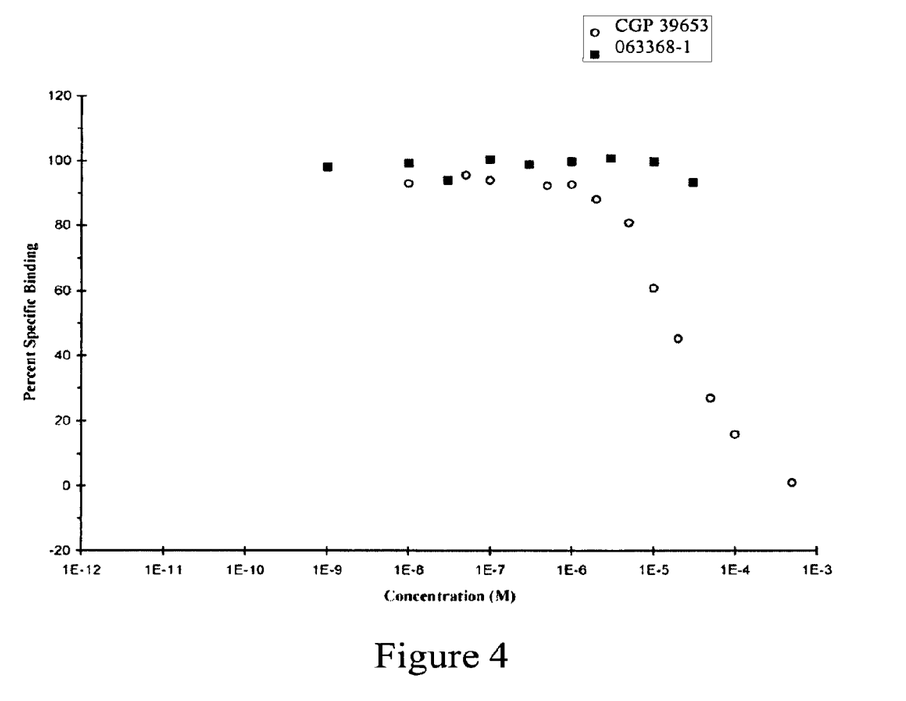
FIG. 4 illustrates non-competition of bicyclo,4-F-PCP with the NMDA receptor competitive antagonist CGP 39653 for binding with the NMDA receptor. In the figure, data corresponding to CGP 39653 are shown as open circles, and data corresponding to bicyclo,4-F-PCP (designated "063368-1" in the figure) are shown as closed squares. The vertical axis represents specific binding percentage, and the horizontal axis represents molar concentration of the respective compound.

As shown in FIG. 4, bicyclo,4-F-PCP does not displace the competitive NMDA receptor agonist CGP 39653. This demonstrates that bicyclo,4-F-PCP does not compete with CGP 39653 (or with NMDA) at competitive sites on the NMDA receptor. This evidence further reinforces the conclusion that bicyclo,4-F-PCP and related compounds are noncompetitive NMDA receptor antagonists.

Example 5 scMET Test for Anti-Convulsive Activity

The subcutaneous metrozol seizure threshold test (scMET) can be used to measure anti-convulsive activity.

For scMET, mice are administered the test compound by i.p. injection of doses of 30, 100 or 300 mg/kg. Metrazol is injected into a loose fold of skin in the midline of the neck at a dose to induce convulsions in 97% of the animals (85 mg/kg). Animals are placed in isolation in cages to minimize stress and observed for 30 min for the presence or absence of a seizure. An episode of clonic spasms, for approximately 3-5 seconds, of the forelimbs, hindlimbs, jaws or vibrassae is taken as the endpoint. Animals which do not meet this criterion are considered protected.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A method of treating a subject afflicted with an ailment selected from the group consisting of retinal disorders, neurofibromatoses, colon tumors, breast tumors, lung tumors, thyroid tumors, and glial tumors the method comprising:
administering to the subject, for a time and in an amount sufficient to alleviate at least one symptom associated with the ailment, an NMDA receptor antagonist having a chemical structure selected from the group consisting of Structures A, B, and C, (A)

(B)

(C)

or an enantiomer, a racemic mixture of enantiomers, a non-racemic mixture of enantiomers, a diastereomer, or a mixture of diastereomers thereof,
wherein R of Structure A is selected from the group consisting a hydroxyl group, an amino group, and a fluorine atom, provided that when R of Structure A is a fluorine atom, the antagonist is an enantiomer of Structure A,
wherein R of Structures B and C is selected from the group consisting of a halo moiety, a nitrate group, a halomethyl group, a nitro moiety, an acyl moiety, a formyl moiety, an alkylsulfonyl moiety, an arylsulfonyl moiety, a cyano moiety, a hydroxyl group, and an amino group, and
wherein one or more hydrogen atoms of the polycyclic ring of the antagonist are independently optionally replaced with a lower alkyl group.

2. The method of claim 1, wherein R of Structures B and C is selected from the group consisting of a fluorine atom, a chlorine atom, a bromine atom, an iodine atom, a nitrate group, and a fluoromethyl group.

3. The method of claim 1, wherein R of Structures B and C is selected from the group consisting of a trifluoromethyl group, a difluoromethyl group, and a monofluoromethyl group.

4. The method of claim 1, wherein one or more hydrogen atoms of the polycyclic ring of the antagonist is replaced with a lower alkyl group.

5. The method of claim 1, wherein one or more hydrogen atoms of the polycyclic ring of the antagonist are independently replaced with a moiety selected from the group consisting of an ethyl group and a methyl group.

6. The method of claim 1, wherein the antagonist is administered to the subject in the form of a pharmaceutically acceptable salt.

7. The method of claim 1, wherein the antagonist is administered to the subject as a pharmaceutical composition comprising the antagonist and a pharmaceutically acceptable carrier.

8. The method of claim 1, wherein the subject is a human.

9. The method of claim 1, wherein the ailment is selected from the group consisting of macular degeneration, adenocarcinoma tumors, astrocytoma, neuroblastoma, and medulloblastoma/rhabdomyosarcoma.

10. A method of alleviating in a subject at least one symptom associated with an ailment selected from the group consisting of retinal disorders, neurofibromatoses, colon tumors, breast tumors, lung tumors, thyroid tumors, and glial tumors, the method comprising:

administering to the subject, for a time and in an amount sufficient to alleviate the symptom, an NMDA receptor antagonist having a chemical structure selected from the group consisting of Structures A, B, and C, (A)

(B)

(C)

or an enantiomer, a racemic mixture of enantiomers, a non-racemic mixture of enantiomers, a diastereomer, or a mixture of diastereomers thereof, wherein R of Structure A is selected from the group consisting of a hydroxyl group, an amino group, and a fluorine atom, provided that when R of Structure A is a fluorine atom, the antagonist is an enantiomer of Structure A, wherein R of Structures B and C is selected from the group consisting of a halo moiety, a nitrate group, a halomethyl group, a nitro moiety, an acyl moiety, a formyl moiety, an alkylsulfonyl moiety, an arylsulfonyl moiety, a cyano moiety, a hydroxyl group, and an amino group, and wherein one or more hydrogen atoms of the polycyclic ring of the antagonist are independently optionally replaced with a lower alkyl group.

11. A pharmaceutical composition comprising a pharmaceutically acceptable carrier and an NMDA receptor antagonist having a chemical structure selected from the group consisting of Structures A, B, and C, (A)

(B)

(C)

or an enantiomer, a racemic mixture of enantiomers, a non-racemic mixture of enantiomers, a diastereomer, or a mixture of diastereomers thereof, wherein R of Structure A is selected from the group consisting of a hydroxyl group, an amino group, and a fluorine atom, provided that when R of Structure A is a fluorine atom, the antagonist is an enantiomer of Structure A, wherein R of Structures B and C is selected from the group consisting of a halo moiety, a nitrate group, a halomethyl group, a nitro moiety, an acyl moiety, a formyl moiety, an alkylsulfonyl moiety, an arylsulfonyl moiety, a cyano moiety, a hydroxyl group, and an amino group, and wherein one or more hydrogen atoms of the polycyclic ring of the antagonist are independently optionally replaced with a lower alkyl group.

12. The pharmaceutical composition of claim 11, wherein R of Structures B and C is selected from the group consisting of a fluorine atom, a chlorine atom, a bromine atom, an iodine atom, a nitrate group, and a fluoromethyl group.

13. The pharmaceutical composition of claim 11, wherein R of Structures B and C is selected from the group consisting of a trifluoromethyl group, a difluoromethyl group, and a monofluoromethyl group.

14. The pharmaceutical composition of claim 11, wherein one or more hydrogen atoms of the polycyclic ring of the antagonist are independently replaced with a lower alkyl group.

15. The pharmaceutical composition of claim 11, wherein one or more hydrogen atoms of the polycyclic ring of the antagonist are independently replaced with a moiety selected from the group consisting of an ethyl group and a methyl group.

16. The pharmaceutical composition of claim 11, wherein the composition is formulated for an administration route selected from the group consisting of parenteral, oral, buccal, transdermal, rectal, colonic, vaginal, intranasal, and respiratory tract administration routes.

17. The pharmaceutical composition of claim 16, wherein the composition is an oral composition selected from the group consisting of hard or soft gelatin capsules, pills, tablets, elixirs, suspensions, syrups, and inhalations.

18. The pharmaceutical composition of claim 16, wherein the composition is a parenteral composition suitable for administration by intramuscular injection, subcutaneous injection, intradermal injection, or intravenous injection.

19. The pharmaceutical composition of claim 16, wherein the composition is a transdermal composition selected from the group consisting of solutions, suspensions, gels, ointments, and salves.

20. The pharmaceutical composition of claim 11, wherein the composition is a sustained-release formulation.

* * * * *